United States Patent [19]

Peiffer

[11] Patent Number: 4,975,482

[45] Date of Patent: Dec. 4, 1990

[54] VISCOELASTIC FLUIDS FORMED THROUGH THE INTERACTION OF POLYMERIZABLE VESICLES AND ALKYL-CONTAINING POLYMERS (C-2381)

[75] Inventor: Dennis G. Peiffer, East Brunswick, N.J.

[73] Assignee: Exxon Research & Engineering Company, Florham Park, N.J.

[21] Appl. No.: 395,616

[22] Filed: Aug. 18, 1989

[51] Int. Cl.$^5$ .............................................. C08L 43/00
[52] U.S. Cl. ................................................... 524/535
[58] Field of Search ......................................... 524/535

Primary Examiner—Joseph L. Schofer
Assistant Examiner—J. M. Reddick
Attorney, Agent, or Firm—Richard E. Nanfeldt

[57] ABSTRACT

The synthesis, preparation and utilization of vesicle-containing viscoelastic monomer fluids mixed with anionic-alkyl containing copolymers are described. These fluid mixtures possess dramatic rheological behavior at very low concentrations as compared to the two individual components or even in comparison with most conventional water soluble polymers. Marked changes in solution properties are exhibited with minor modification in the structure of the copolymers, monomers, vesicle structure and monomer stoichometry.

In addition, the synthesis, preparation and utilization of a novel family of polymerizable vesicles formed via anionic-cationic interactions are described. These structures are formed under very mild agitation conditions and the resulting solutions possess rheological properties substantially different than either of the individual monomers or conventional polymers formed with these unique monomers. Furthermore these vesicles could be useful in a number of encapsulation schemes.

1 Claim, 10 Drawing Sheets

FIG. 2B
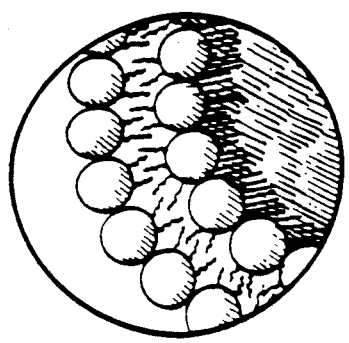
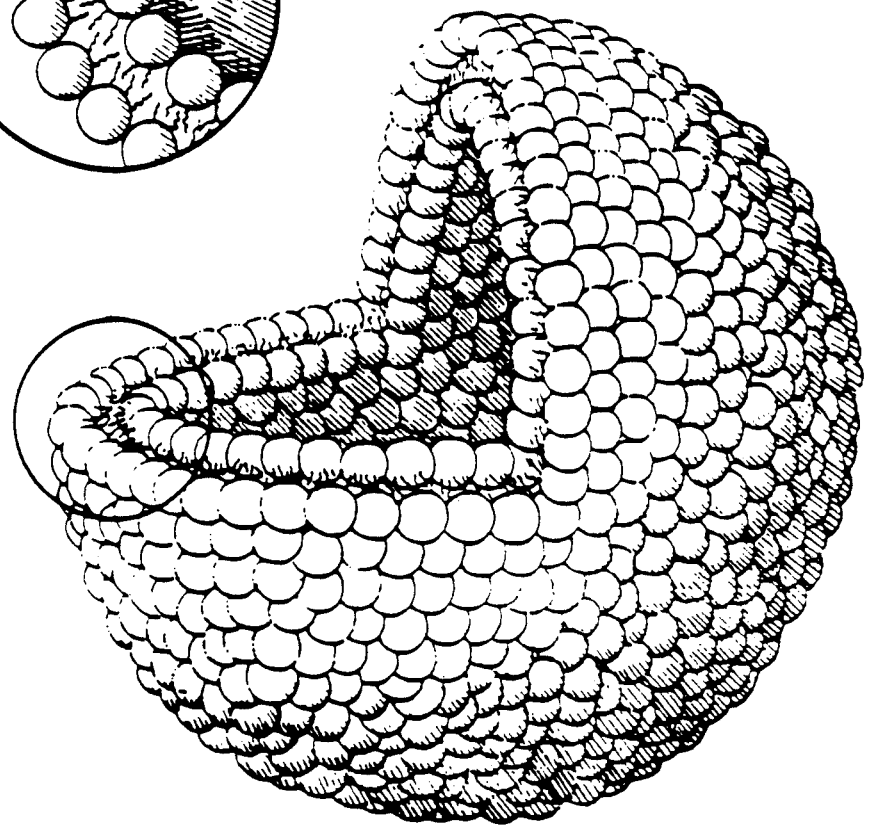
FIG. 2A

VISCOELASTIC FLUIDS FORMED THROUGH THE INTERACTION OF POLYMERIZABLE VESICLES AND ALKYL-CONTAINING POLYMERS (C-2381)

The instant invention describes the synthesis, preparation and utilization of vesicle-containing viscoelastic monomer fluids mixed with anionic-alkyl containing copolymers. These fluid mixtures possess dramatic rheological behavior at very low concentrations as compared to the two individual components or even in comparison with most conventional water soluble polymers. Marked changes in solution properties are exhibited with minor modification in the structure of the copolymers, monomers, vesicle structure and monomer stoichometry.

In addition the synthesis, preparation and utilization of a novel family of polymerizable vesicles formed via anionic-cationic interactions are described. These structures are formed under very mild agitation conditions and the resulting solutions possess rheological properties substantially different than either of the individual monomers or conventional polymers formed with these unique monomers. Furthermore these vesicles could be useful in a number of encapsulation schemes.

BACKGROUND OF THE INVENTION

Macromolecular materials are very useful as viscosification agents when dissolved in an appropriate solvent system. The major reason for this viscosity enhancement is due to the very large dimensions of the individual polymer chain. Any increase in the size of the polymer chain will produce a corresponding enhancement in the viscosity of the solution. This effect is maximized when the polymer is dissolved in a "good" solvent. Therefore, in general, a hydrocarbon soluble polymer is useful for thickening hydrocarbon solvents, while a water soluble polymer is appropriate for increasing the viscosity of aqueous systems. With regard to aqueous solutions, water soluble nonionic polymers and high charge density sulfonated or carboxylated polyelectrolytes are quite useful in this regard and are commonly used materials. However, the solution properties of the former family of materials are controlled primarily through modification of the molecular weight of the polymer and through changes in the level of dissolved polymer. These materials become especially effective at concentrations where the individual polymer chains begin to overlap. This "transition" is commonly referred to in the literature as the chain overlap concentration or simply $C^*$. It should be noted that in most nonionic polymers of commercial interest, a relatively large amount of polymer is required in order to reach the required viscosity level.

This approach is undesirable from an economic viewpoint.

In this instant invention is described the finding that a novel family of cationic-alkyl containing monomers intimately mixed with a family of anionic-alkyl containing monomers, i.e. both polymerizable moieties, form large structures in solution. The dimensions of these structures are comparable or larger than polymeric chains. As a result, these structures termed vesicles, formed from these monomers are useful and very effective viscosifiers for aqueous solutions. In addition, these monomer mixtures have markedly unique and improved solution properties, as compared to conventional water soluble polymers. These fluids formed with the monomer mixtures can adequately be described as polymerizable vesicle fluids.

In addition, these unusual and novel interactions opens up a potentially interesting area in the utilization of these specific structures in a number of areas including oil field chemicals, encapsulation procedures, drug delivery, lubrication, shear thickening drilling fluids and the like.

Furthermore, in this instant invention is described the finding that again a novel family of cationic-alkyl containing monomers intimately mixed with a family of anionic-alkyl containing monomers, i.e., both polymerizable moieties, form large structures in solution. The dimensions of these structures are comparable or larger than polymeric chains. An intimate mixture of these structures with a water soluble copolymer containing long alkyl groups produce a novel viscoelastic fluid. It is important to note that the alkyl group, i.e. hydrophobic moiety, is an essential requirement for the effective utilization of this invention. In essence, the long alkyl groups of preferentially interacts, i.e., compatabilized, with the vesicle bilayer structure This interaction allows the alkyl-containing polymer to interact with a number of individual vesicles. As a result, a dynamic three-dimensional structure of vesicles are formed "tied" together via the long polymer chains.

These copolymers are based on, but not limited to, the incorporation of the above alkyl-containing monomers into an acrylamide backbone structure. Furthermore, these vesicles are based on, but not limited to, the mixture of polymerizable cationic and polymerizable anionic monomer units.

SUMMARY OF THE INVENTION

A process for producing highly viscoelastic and highly effective rheological control agents through the intimate mixing of a cationic and anionic monomer entities to form a vesicle structure in solution and an anionically-charged hydrophobically interacting polymer. The process relies on the addition of hydrophobically-associating water soluble polymers to a solution containing the vesicles fluid (and vice versa). Both individual components in water produce a clear, uniform and homogeneous solution as does the intimate mixture of the two components. Furthermore, the individual components by themselves give to aqueous solutions a number of technologically important attributes such as shear thickening, salt insensitivity, emulsification properties and the like. However, the process of mixing the two individual components results in a clear, homogeneous solution that has superior properties to either component and permits one to have a markedly improved degree of control of the rheological properties of aqueous media.

BRIEF DESCRIPTION OF THE DRAWINGS

FIG. 2 illustrates a schematic drawing showing the external and internal structure of the polymerizable vesicles entity.

DETAILED DESCRIPTION OF THE INVENTION

Figure 1:
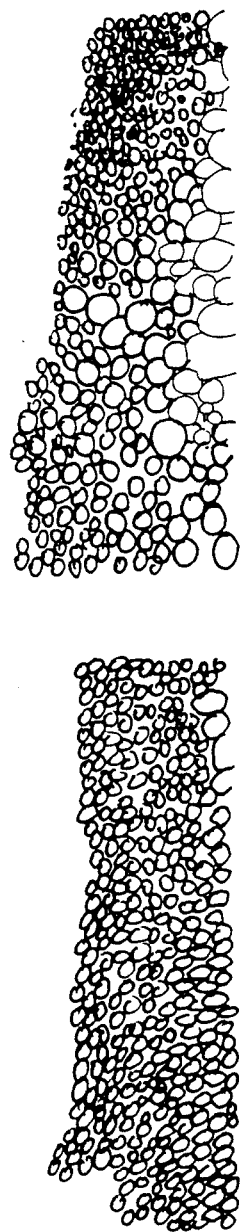
FIG. 1 illustrates photomicrographs showing the typical spherical structure of the vesicles in an aqueous media.

The process of this invention markedly enhances the rheological properties of aqueous media as just described. In particular, it enables one to control solution properties by mixing a water soluble monomer, acrylamide, and water soluble monomers such as an amidoalkyl sulfonate to give copolymers which alone are efficient aqueous viscosifiers with a vesicle fluid which also alone are very effective rheological control additives. The resultant intimate mixture now possess properties that are completely different and superior to that of the individual components. With regard to the above copolymers, the process relies on the solubility of the alkyl derivatives into a predominantly aqueous media. These anionic derivatives form micelles without the utilization of any other surfactant. The reaction mixture is isotropic, clear, and homogeneous.

These micellar reaction mixtures are free of visible oil droplets or particulates of the water insoluble monomer. The polymerization can therefore be initiated by water soluble initiators to give copolymers that are substantially free of visible particulates. The resultant reaction product remains homogeneous throughout the course of the reaction.

Mieelles formed by the anionic (sulfonate) monomers which are water soluble are generally very small aggregates which consist of on the order of 50 to 200 molecules. They form spontaneously upon mixing the components together, i.e., they do not require the vigorous mixing conditions required in conventional emulsion polymerization in which macroemulsions are formed. The macroemulsion droplets of the conventional emulsion polymerization process have diameters which are at least 10,000 Å. They therefore tend to phase separate upon standing, leading to undesirable inhomogeneities in the produced copolymer. The homogeneous micellar reaction mixture is, on the other hand, much more stable against demixing than the formulations used in emulsion polymerization processes. Indeed, no stirring is required during the course of the micellar copolymerization - the micellar aggregates remain extremely finely dispersed throughout. Moreover, the extremely dispersed nature of the micellar aggregate permits the copolymerization to occur in such a way that water soluble copolymer is produced which does not contain particulates or latexes of water insoluble polymers. These would be detrimental in such applications as secondary oil recovery, which requires a product which is substantially free of pore plugging particulates.

An additional important feature is that the resultant copolymer has possessed both a anionic charge and a hydrophobic unit on the polymer chain without the necessity of further chemical post-treatment. Besides the ease of polymerization to form these hydrophobically associating polymers, the anionic and alkyl group, hydrophobic entity, gives one a great degree of control of the final polymer structure and of course, physical properties.

Surfactants, although unnecessary as described above, can still be used. The surfactants which may be used in this process may be one of the water soluble surfactants such as salts of alkylsulfates, sulfonates, carboxylates and the like, or nonionic such as ethylene oxide-propylene oxides copolymers, or polyoxyethylene alkyl ethers, etc. or cationic surfactants such as primary alkylamines, dialky secondary amines, or ethoxylated fatty amines. Suitable surfactants may be chosen from these on the basis of water solubility and solubilization capacity for any other water insoluble monomers intentionally added to the polymerization mixture.

Suitable free radical initiators for the copolymerization process are peroxides such as hydrogen peroxide, potassium persulfate, alkyl peroxides and the like. The concentration of the free radical initiator is about 0.01 to about 0.50 grams per hundred grams of acrylamide and alkylacrylamide monomer. The polymerization is conducted in the absence of oxygen at a temperature of about 20° to about 100° C. The polymer may be recovered from the reaction mixture by precipitation by non-solvents such as acetone.

It should be pointed out that neither the mode of polymerization (solution, suspension, or emulsion, microemulsion or micellar polymerization technique and the like), nor the initiation is actually provided that the method or the products of initiated step does not inhibit or chemically modify the initial polymer molecular structure of reacting monomers.

The water soluble copolymers which are produced by the copolymerization processes the instant invention are characterized by the formula

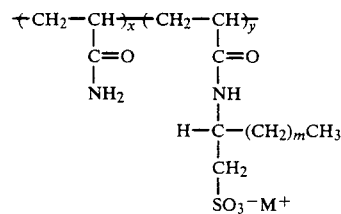

wherein m is preferably 6 to 22 more preferably 6 to 20 and most preferably 6 to 18. Typical, but non-limiting examples of preferred alkyl groups are hexyl, octyl, decyl, dodecyl and steryl groups. x is preferably about 90.0 to 99.9 mole %, more preferably about 95.0 to about 99.8 mole %, and most preferably about 97.0 to about 99.5 mole %. y is about 10.0 to about 0.1 mole %, more preferably about 5.0 to about 0.2 mole %, and most preferably about 3.0 to about 0.5 mole %. These water soluble copolymers are of a sufficiently high molecular weight that they are efficient viscosifiers of water or brine, but not so high that they are readily susceptible to irreversible shear degradation. That is, their intrinsic viscosity is greater than 1 dl/g and less than about 10 dl/g. M is a tertiary amine or a metal cation selected from the group consisting of aluminum and lead Groups IA, IIA, IB and IIB of the Periodic Table of Elements.

The water soluble terpolymers which are produced by the copolymerization process of the instant invention are characterized by the formula:

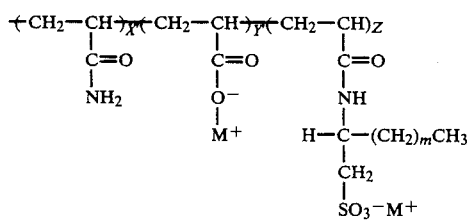

wherein m is preferably 6 to 22 more preferably 6 to 20 and most preferably 6 to 18. Typical, but nonlimiting examples of preferred alkyl groups are hexyl, octyl, decyl, dodecyl and hexadecyl groups. X' is preferably about 90.0 to about 99.9 mole %, more preferably about 95.0 to about 99.8 mole %, and most preferably about 97.0 to about 99.5 mole % and X' = 100 - (Y' + Z) wherein Z is about 0.1 to about 10.0 mole %, more preferably about 0.2 to about 5 and most preferably about 0.3 to 3.0. These water soluble copolymers are of a sufficiently high molecular weight that they are efficient viscosifiers of water or brine, but not so high that they are readily susceptible to irreversible shear degradation. That is, their intrinsic viscosity is greater than about 1 dl/g and less than about 10 dl/g. M is a tertiary amine or a metal cation selected from group consisting of aluminum, iron, lead, Groups IA, IIA, IB and IIB of the Periodic Table of Elements.

With regard to the second component of this mixture, i.e., the vesicle fluid, we note that the particular structures formed via mixing monomers derived from the reaction of an alkyl halide with N,N-dimethyl alkylamines and the amidoalkylsulfonate monomer are spherical in nature and as a result aqueous solutions containing these structures have properties comparable to relatively high molecular weight polymers. These structures form without the utilization of any other surfactant.

The process relies on the appropriate choice of an anionic counterion (on the sulfonate monomer) which is attracted to the cationic charge on the cationic monomer or vice versa. The counterion possess relatively long alkyl groups and surprisingly form the spherical structures resulting in solution properties comparable to polymeric solutions.

These fluids have solution properties comparable to excellent water soluble polymeric viscosifiers. It should be noted that dilute solutions of ionic and nonionic surfactants and detergents usually behave as Newtonian liquids i.e., viscoelastic behavior is rare.

A criterion for the formation of these polymerizable vesicle aqueous fluids can be approximated with the theoretical considerations of D. J. Mitchell and B. W. Ninham. J. Chem. Soc., Faraday Trans. 2, 77, 601 (1981) and J. N. Israelachvili, D. J. Mitchell and B. W. Ninham, J. Chem. Soc., Faraday Trans. 2, 72, 1525 (1976). The first consequences of packing conditions of these cationic monomers with the appropriate anionic counterion (or vice versa) are applied under the assumptions of (1) constant volume v per monomer molecule and (2) constant headgroup area $a_o$ for a monomer molecule In general, since the radius of the sphere (i.e. bilayer) cannot exceed a certain critical length, $l_c$, roughly equal to but less than the fully extended length of the hydrocarbon, i.e. alkyl, group. It is shown by relatively simple packing considerations that spherelike structures are able to form when the relationship $v/a_o l_c \approx 1.0$, is approximately found.

The water soluble polymerizable anionic and cationic monomers which produce these spherical aqueous fluids of the instant invention are characterized by the formula mixture of:

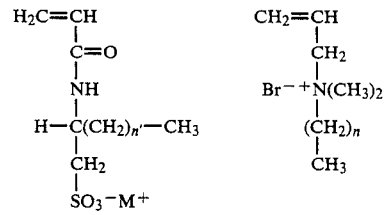

wherein n and n' is preferably 6 to 22 straight chained or branch chained alkyl or cycloalkyl group, more preferably 8 to 20 and most preferably 8 to 18. Typical, but not limiting examples of preferred alkyl groups are hexyl, octyl, decyl, dodecyl and stearyl groups, wherein the ratio of the cationic to anionic monomer is about 1.1/1 to 1/1.1 more prefer ably about 1/1.

An aqueous solution comprising
(a) water
(b) about 0.1 to about 20.0 wt.% of a mixture of a visocelastic monomer fluid and an anionic-alkyl containing copolymer, wherein said viscoelastic monomer fluid is a mixture of a cationic monomer and an anionic monomer characterized by the formula:

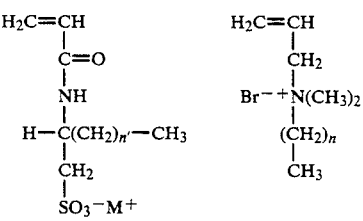

wherein n' and n are both a 6 to 22 and a ratio of the cationic monomer to the anionic monomer is about 1.1/1 to 1/1.1; wherein the anionic alkyl containing copolymer is characterized by the formula:

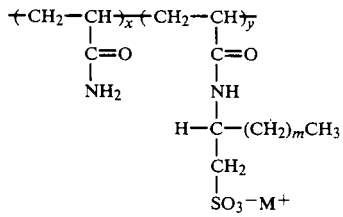

wherein m is preferably 6 to 22 and x is about 90.0 to 99.9 mole % and y is about 10.0 to about 0.1 mole %, and $M^+$ is a tertiary amine or a metal cation selected from the group consisting of aluminum, lead and Groups IA, IIA, IB and IIB of the Periodic Table of Elements, wherein the weight ratio of the viscoelastic monomer fluid to the anionic alkyl containing a polymer is about 1.1/1 to 1/1.1.

An aqueous solution comprising
(a) water
(b) about 0.1 to about 20.0 wt.% of a mixture of a viscoelastic monomer fluid and an anionic-alkyl containing terpolymer, wherein said viscoelastic monomer fluid is a mixture of a cationic monomer and an anionic monomer characterized by the formula:

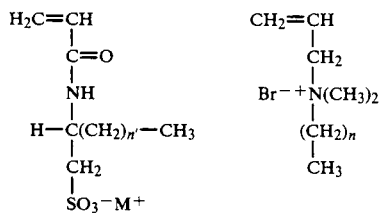

wherein n' and n are both preferably 6 to 22 wherein $M^+$ is selected from the group consisting of Groups IA, IIA, IB and IIB of the Periodic Table of Elements and a ratio of the cationic monomer to the anionic monomer is about 1.1/1 to 1/1.1; wherein the anionic alkyl containing terpolymer is characterized by the formula:

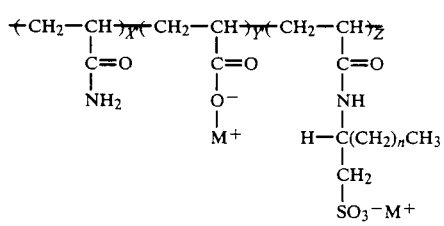

wherein n is preferably 6 to 22 X' is preferably about 90.0 to about 99.9 mole %, X' = 100 - (Y'+Z) wherein Z is about 0.1 to about 10.0 mole%, M is a tertiary amine or a metal cation selected from group consisting of aluminum, iron, lead, Groups IA, IIA, IB and IIB of the Periodic Table of Elements, wherein the weight ratio of the viscoelastic monomer fluid to the anionic alkyl containing terpolymer is about 1.1/1 to 1/1.1.

DESCRIPTION OF THE PREFERRED EMBODIMENT

Example 1

Synthesis of Anionic-Hydrophobic Monomer

A representative example for the synthesis of the following monomer structures which are subsequently copolymerized to form a lightly sulfonated (anionic) alkyl-containing water soluble copolymer is described below.

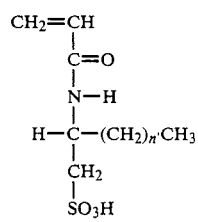

In this representative example n' = 9.

Into a 1 liter-4 neck round bottom flask add 300 mls of 1,2 dichloroethane and the following.
42.0 g of dodecene-1 (0.25 mole)
27.5 g of acrylonitrile (0.50 mole)
3.3 g of triethylphosphate (0.02 mole)

Cool mixture to approximately 0° C. Into a dropping funnel add 100 mls of 1,2 dichloroethane into which 8.0 g of sulfur trioxide (0.1 mole) had been dissolved. Carefully add dropwise this solution to the previously described cooled mixture. Keep the temperature about 0° C. with agitation until all of the sulfur trioxide solution has been added. Now allow the temperature of the mixture to rise to room temperature. In most instances, a fine, lightly yellow precipitate forms immediately and slowly settles to the bottom of the flask. This precipitate is filtered and washed with excess 1,2 dichloroethane and the lightly yellow precipitate turns a white color. The precipitate is subsequently dried in a vacuum oven at room temperature for about 24–48 hours. Elemental and NNR analysis confirms that the monomer is very pure (>99%) and has, in this specific example, the following molecular structure.

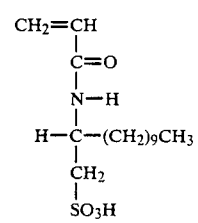

These monomeric materials can subsequently be neutralized with a large variety of materials via classical acid-base neutralization schemes.

Example 2

Synthesis of Anionic-Hydrophobic Monomer (Alternate Synthesis)

A representative example for the synthesis of the following monomer structure which are subsequently copolymerized to form a lightly sulfonated (anionc) alkyl-containing water soluble copolymer is described below:

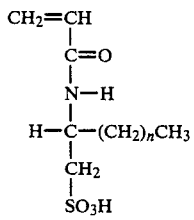

In this representative example n=9.

Into a 1 liter-4 neck round bottom flask add 300 mls of 1,2 dichloroethane and the following.
  42.0 g of dodecene-1 (0.25 mole)
  27.5 g of acrylonitrile (0.50 mole)
  3.3 g of triethylphosphate (0.02 mole)

Cool mixture to approximately 0° C. Into a dropping funnel add 100 mls of 1,2 dichloroethane into which 9.0 g of sulfur trioxide (0.1 mole) has been dissolved. Carefully add dropwise this solution to the previously described cooled mixture. Keep the temperature about 0° C. with agitation until all of the sulfur trioxide solution has been added. Now allow the temperature of the mixture to rise to room temperature. In most instances, a fine, lightly yellow precipitate forms immediately and slowly settles to the bottom of the flask. This precipitate is filtered and washed with excess 1,2 dichloroethane and the lightly yellow precipitate turns a white color. The precipitate is subsequently dried in a vacuum oven at room temperature for about 24-48 hours. Elemental and NMR analysis confirms that the monomer is very pure (>99%) and has, in this specific example, the following molecular structure.

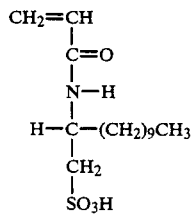

Again these monomeric materials can subsequently be neutralized with a large variety of materials via classical acid-base neutralization schemes.

Example 3

Copolymer Synthesis

A representative example for the synthesis of an acrylamide copolymer containing the above described monomer (n=9) is described below.
  Into a 1 liter-4 neck round bottom flask add:
  300 mls distilled water
  47.0 g acrylamide (99 mole %)
  2.62 g sulfonate-alkyl (n=9) containing monomer (1 mole %)
  0.35 g sodium hydroxide
  0.05 g potassium persulfate The solution is purged with argon gas for approximately two hours at room temperature and subsequently the temperature is elevated to 50° C. After 24 hours, the copolymer is precipitated from solution with a large excess of acetone. Subsequently, the copolymer is washed several times with acetone and dried in a vacuum over at 50° C. for 24 hours. Elemental analysis, i.e., sulfur content, showed that the copolymer contained 0.92 mole % of the sulfonate-alkyl containing monomer units. This copolymer is designated as 11868-47BR.

Example 4

Hydrolysis

A typical example for the hydrolysis of the acrylamide-sulfonate alkyl containing copolymer is described below.

Into a small flask is dissolved with continuous agitation, 1 g of the previously synthesized copolymer (n=9) into 200 mls of distilled water. Subsequently 0.22 g of sodium hydroxide is added and the solution temperature increased from 40°-55° C. for 24 hours. The hydrolyzed copolymer is precipitated from solution with a large excess of acetone and then again thoroughly washed with a large excess of acetone. The precipitate is dried in a vacuum oven at 40° C. for 48 hours. This recovery procedure is repeated several times with only a minor change in the final elemental analysis results. The detailed hydrolysis results performed on the previously described copolymers is presented in Table I.

TABLE I

Hydrolysis Conditions and Final Hydrolysis Levels on a Acrylamide: Alkyl Sulfonate Containing Copolymer

| Designation | Sodium Hydroxide (g) | Sulfonate Content (mole %) | Hydrolysis (mole %) |
| --- | --- | --- | --- |
| 47BR | 0 | 0.92 | 0 |
| 47BRH1 | 0.028 | 0.94 | 6.8 |
| 47BRH2 | 0.056 | 0.92 | 7.8 |
| 47BRH3 | 0.11 | 0.96 | 15.6 |
| 47BRH4 | 0.17 | 0.93 | 24.1 |
| 47BRH5 | 0.22 | 0.91 | 30.9 |
| 47BRH6 | 0.44 | 0.92 | 38.9 |

It should be noted that under these relatively mild hydrolysis conditions, it is clearly observed that the level of hydrolysis is markedly modified with increasing levels of added base, i.e. sodium hydroxide. In addition, it is noted that the sulfonation level and therefore, the alkyl group level remains invariant even up to high levels of hydrolysis. Therefore, the rheology of solutions containing these polymers can be compared since both the degree of polymerization and alkyl group concentration is also invariant under these hydrolysis conditions. Alternatively, acrylic acid, methacrylic acid and the like can also be used to introduce carbonyl groups into the polymer structure.

Example 5

Cationic-Hydrophobic Monomer

Three representative examples for the synthesis of the following monomer structures to form these cationic viscoelastic monomer fluids is described below:

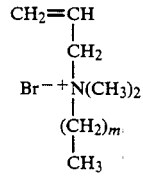

In these representative examples n=18 (11868-106A), n=13 (11868-106B) and n=17 (11868-106C).

Into a small round bottom flask add the following materials together and heat to 50° C. for four hours:

| | |
|---|---|
| 11868-106A | 14.2 g allyl bromine |
| | 31.6 g N,N-dimethyl dodecylamine |
| 11868-106B | 14.2 allyl bromide |
| | 28.3 g N,N-dimethyl tetradecylamine |
| 11868-106C | 14.2 g allyl bromine |
| | 34.9 g N,N-dimethyl octadecylamine |

The monomers are further purified through conventional analytical techniques. Elemental and NMR analysis confirms that the monomers are very pure (>99%) and has, in these specific examples, the following molecular structure:

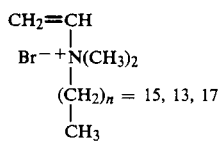

Example 6

Preparation of Polymerizable Vesicle Fluids

Representative examples for the preparation of polymerizable vesicle fluids containing the described families of synthesized anionic and cationic monomers are briefly described below.

Dissolve the monomers into water and subsequently mix the two fluids together. It is noted that the requirement that a stoichometric amount of the monomers be used is not a necessary requirement. As we will observe, a relatively broad range of these materials can be used for effective utilization and preparation of these unique fluids. However, stoichometric amounts of these compounds are used in a number of the examples presented in this patent for illustrative purposes only. In any event, the viscosity of the fluid immediately increases to a value dependent upon the nature and concentration of the two monomers. Moreover, it is noted that the structures formed via this method are produced under rather mild agitation conditions. Finally it is noted that the structures formed via this method are produced for example, under relatively mild agitation conditions (i.e. magnetic stirring procedures).

In the example shown in this instant invention, 11868-124C represents the mixing of 1 g of 11868-106C cationic monomer with 0.525 g of 11868-94A anionic monomer in 40 mls of distilled water. The complete synthesis, preparation and utilization of the resulting aqueous fluids are presented within the instant invention.

Example 7

Solution Characteristics

It is anticipated that the morphology that these monomer mixtures can assume in solution is quite complex and undoubtedly, the dynamics of these structures can change rapidly with time, temperature, stress, strain rate, pressure, ionic strength and the like. However, our initial findings indicate that the monomer mixtures form relatively large spherical structures as shown in photomicrographs in FIG. 1. A large number of "single" and "overlapping" spheres can be seen due to the high concentration of spheres within the field of view. Our findings further confirm that the interior structure of each sphere can be adequately represented as a vesicle with the membrane possessing a bilayer structure. The internal and continuous phase in such a structure is the aqueous solvent itself.

In FIG. 2, the spheres represent both the vinyl "head" group and the anionic-cationic region of the monomers. These latter groups interact strongly through charge attraction potentials forming a dialkyl-type moiety. The alkyl "tails" are embedded in the bilayer interior due to the well-known hydropholic interaction. This is a facile way of forming bilayer structures since very mild agitation (in some cases no agitation is required) conditions are necessary. In addition, it is a relatively simple matter to modify the structure of either the head group area and/or alkyl tails individually and combining these individual structures to form a dialkyl structure not readily obtainable via modification of a covalently bonded dialkyl structure. In addition, it should be noted that these vesicle structures are polymerizable and therefore, the vesicle structure is "permanently" fixed via these covalent bonds.

The rheological properties of these vesicle-containing fluids are controlled to a large degree by the large dimensions of the individual spheres and their interactions, i.e. charge-charge and the like.

It should be noted, however, that the complete verification of the morphology of these solutions does not in anyway detract from the utilization of the novel properties of these vesicle containing fluids.

Example 8

Rheology

Figure 3:
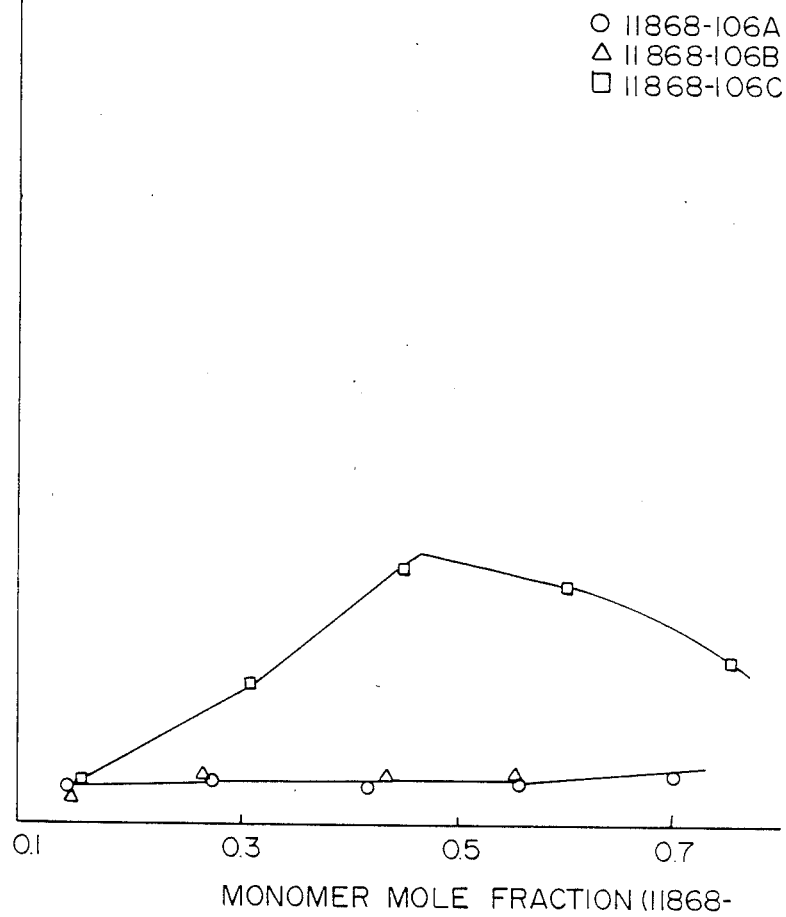
FIG. 3 illustrates viscosity-composition curves of a 2 g/dl monomer mixture of 11868-76B anionic monomer with 11868-106A, B and C cationic monomers.
Figure 4:
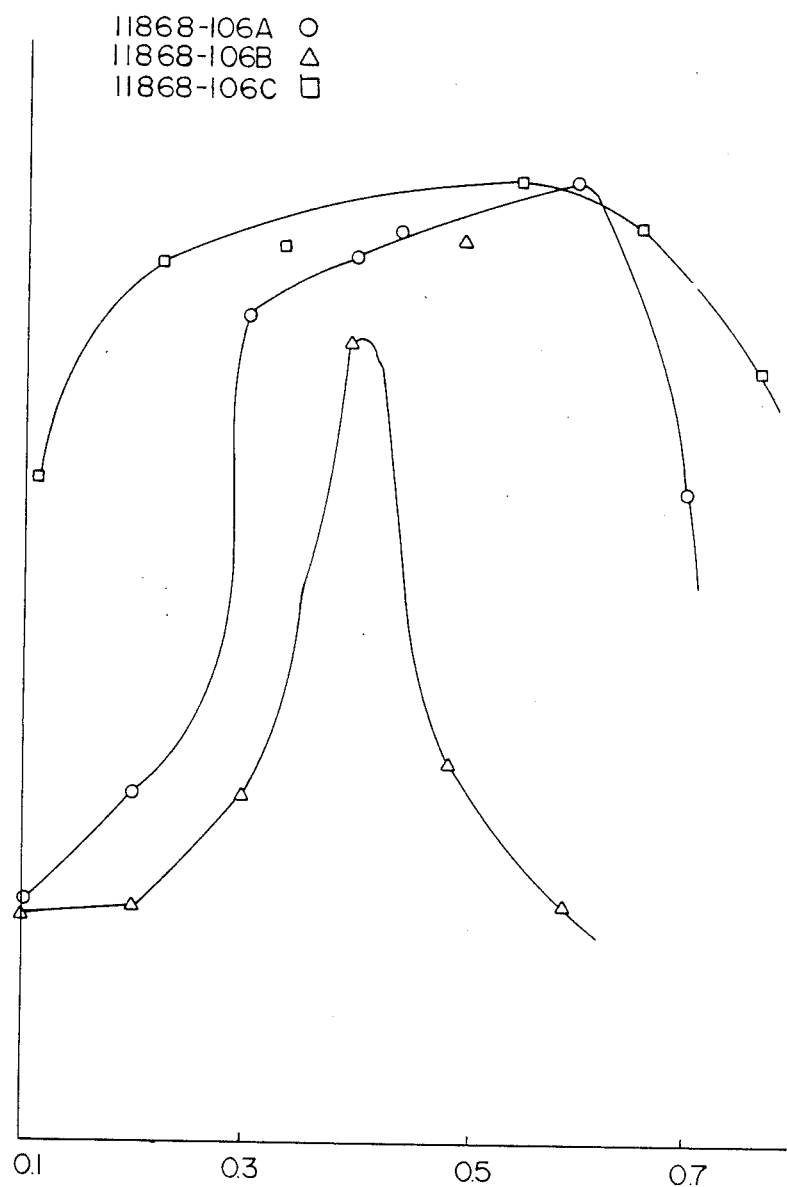
FIG. 4 illustrates viscosity-composition profiles of a 2 g/dl vesicle fluid composed of the anionic 11868-94A monomer with the cationic monomers 11868-106A, B, and C.
Figure 5:
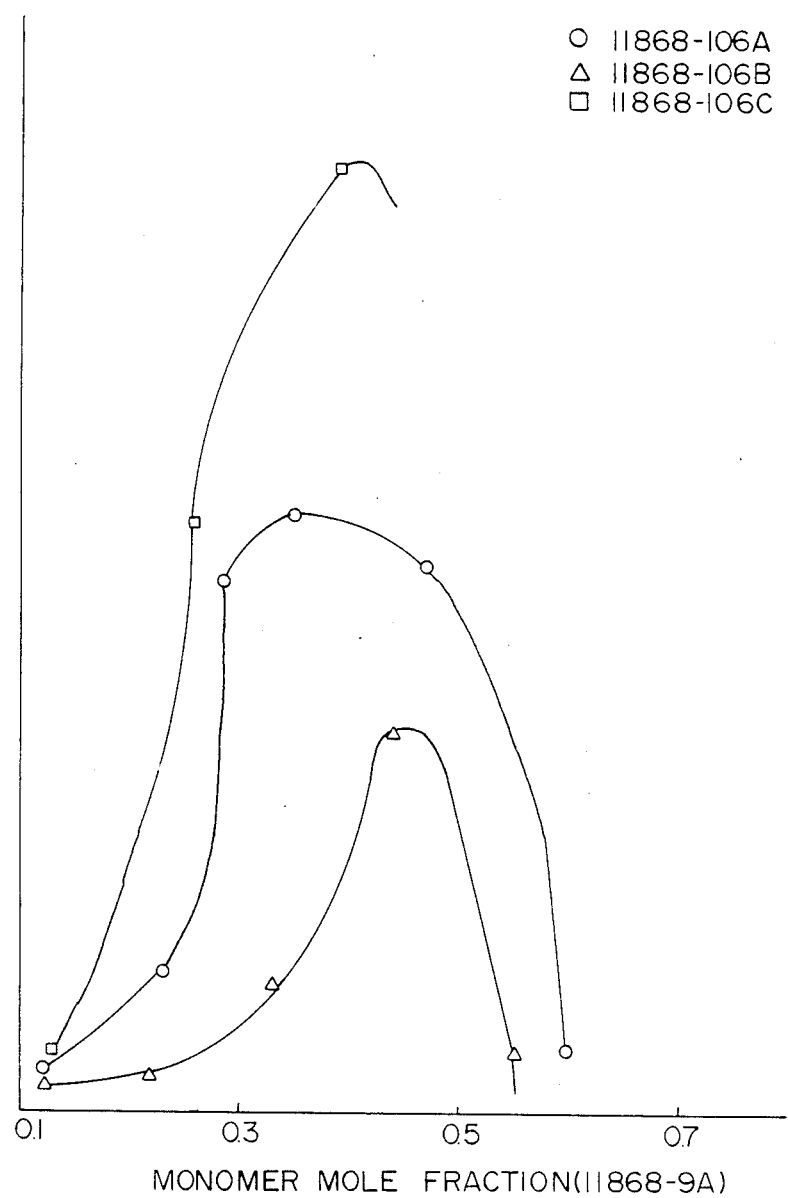
FIG. 5 illustrates viscosity-composition profiles of a 2 g/dl vesicle fluid composed of the anionic monomer 11868-9A with the cationic monomers 11868-106A, B and C.

FIGS. 3-5 shows some representative rheological properties of the above described cationic monomers, i.e. 11868-106A,B,C mixed with a number of anionic (sulfonate-containing) monomers previously described in this application. Again these latter monomers have essentially identical molecular structures with only relatively minor changes in the length of the alkyl group, i.e. n=5 (11868-76B), n=9 (11868-9A) and n=13 (11868-94A)

It is noted that each figure corresponds to the addition of a specific anionic monomer to the three cationic monomers An examination of the data in FIGS. 3-5 clearly confirms 1. Even though the molecular weight of the individual monomer units is quite low (<1000 g mole$^{-1}$, in general), the rheological properties of the fluid containing these monomers display high molecular weight polymeric properties.
2. At relatively low monomer concentrations, very dramatic viscosity values are achievable.
3. With a specific anionic monomer of a characteristic alkyl length (n), the viscosity rises with increases in the alkyl length of the cationic monomer units and vice versa.
4. A maximum in the viscosity is observed, in general, at a specific stoichometric ratio of the anionic/cationic monomer units.
5. At high shear rates, shear thinning characteristics are generally observed.
6. At low shear rates, marked time dependencies of the rheological properties are sometimes found.

7. Dilution causes a reduction in the magnitude of the rheological properties.

In summary the synthesis, preparation and utilization of polymerizable vesicles formed via anionic/cationic interactions and fluid compositions can impart improved and useful rheological properties to aqueous fluids. The specific properties can be varied over a very broad range due to the ability to readily modify or change a number of compositional variables within the monomers comprising the monomer mixture.

These types of monomer containing aqueous viscoelastic fluids are useful a rheological control additives in a variety of drilling operations. Included in this category are a variety of well control and workover fluids, fracturing fluids, brine viscosifiers, gelation agents, foaming additives, completion fluids, enhanced oil recovery, drag reduction agents and the like.

In addition, these vesicle-containing fluids are excellent candidates for a variety of encapsulation procedures encompassing oil field chemical applications, drug delivery, fertilizer encapsulants, lubrication, printing and the like.

Example 9

Figure 6:
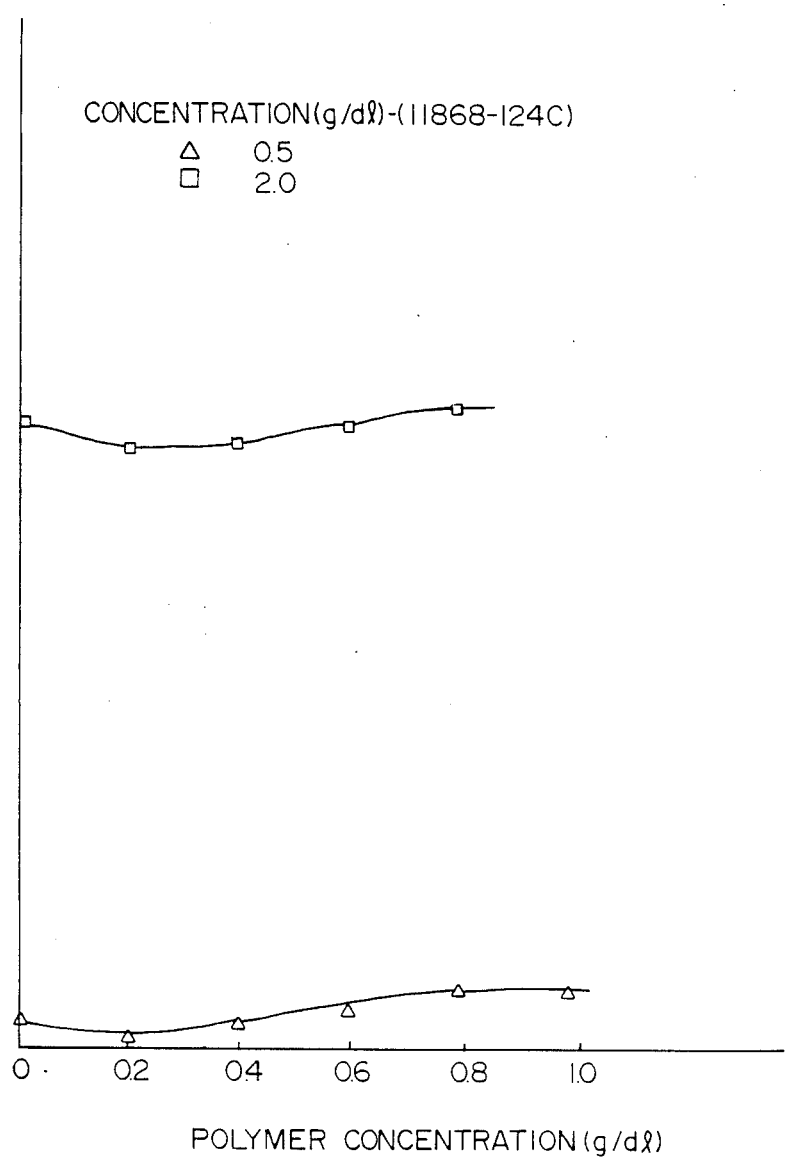
FIGS. 6 illustrates the effect of the addition of 11868-47BR copolymer to 11868-124C solution (i.e. vesicle-containing solution).
Figure 7:
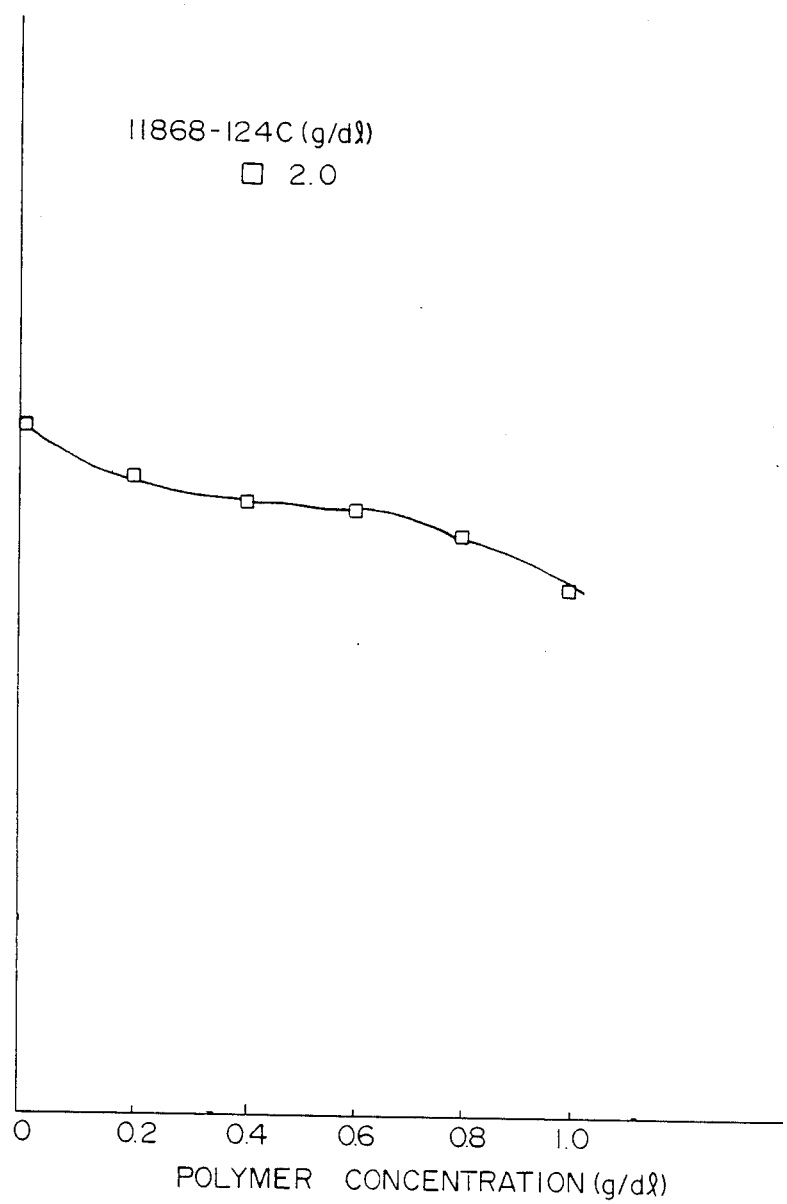
FIG. 7 illustrates the effect of the addition of 11868-47BRH5 terpolymer to 11868-124C solution (i.e. vesicle-containing dsolution).
Figure 8:
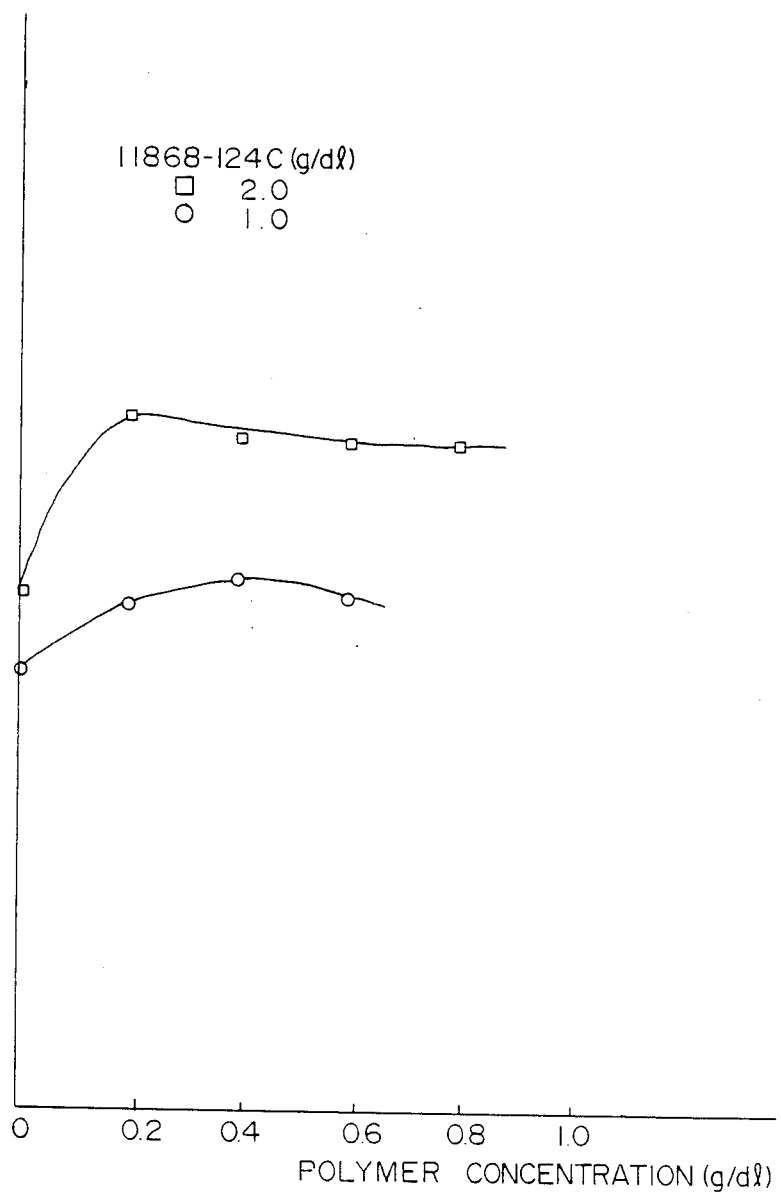
FIG. 8 illustrates the effect of the addition of 11868-47BR copolymer to a sonicated 11868-124C solution (i.e. vesicle-containing solution).

FIGS. 6-8 shows some representative rheological properties of the above described mixtures of vesicle-containing fluids (i.e. 11868-124C) mixed with a number of unhydrolyzed and hydrolyzed anionic (i.e. sulfonate-containing) monomers (i.e. 11868-47BR and 11868-47BRH5). In these specific figures the viscosity is plotted as a function of polymer concentration, was varied over a more limited range.

An examination of the data in these figures clearly show:

1. Even though the molecular weight of the individual monomer units is quite low ($< 100$ g mole$^{-1}$), in general), the rheological properties of the fluid containing these monomers display high molecular weight polymeric properties. This is clearly due to the large dimensions of the vesicles themselves.
2. At low monomer concentration, dramatic viscosity values are achievable.
3. A modest increase in viscosity is found with the addition of relatively small amounts of the unhydrolyzed copolymer (FIG. 6).
4. Dilution causes a reduction in the magnitude of the rheological properties, in general.
5. A large decrease in viscosity is noted with the addition of relatively small amounts of the hydrolyzed copolymers (FIG. 7). The rate of decrease in properties is a strong function of the hydrolysis level.
6. Sonication of the 11868-124C vesicle-containing solution produces a reduction in the vesicle size. A reduction in the viscosity is correspondingly observed.
7. If the distance between vesicles are not too large and their size is roughly comparable to the dimensions of the above described copolymers, then a dramatic rise in viscosity is observed (FIG. 8). In specific instances, several orders of magnitude increase is found.
8. If the dimensions of the vesicle are large as compared to those of the above described copolymers, then relatively modest increases in viscosity are observed
9. In most instances, shear thinning characteristics are found.

Figure 9:
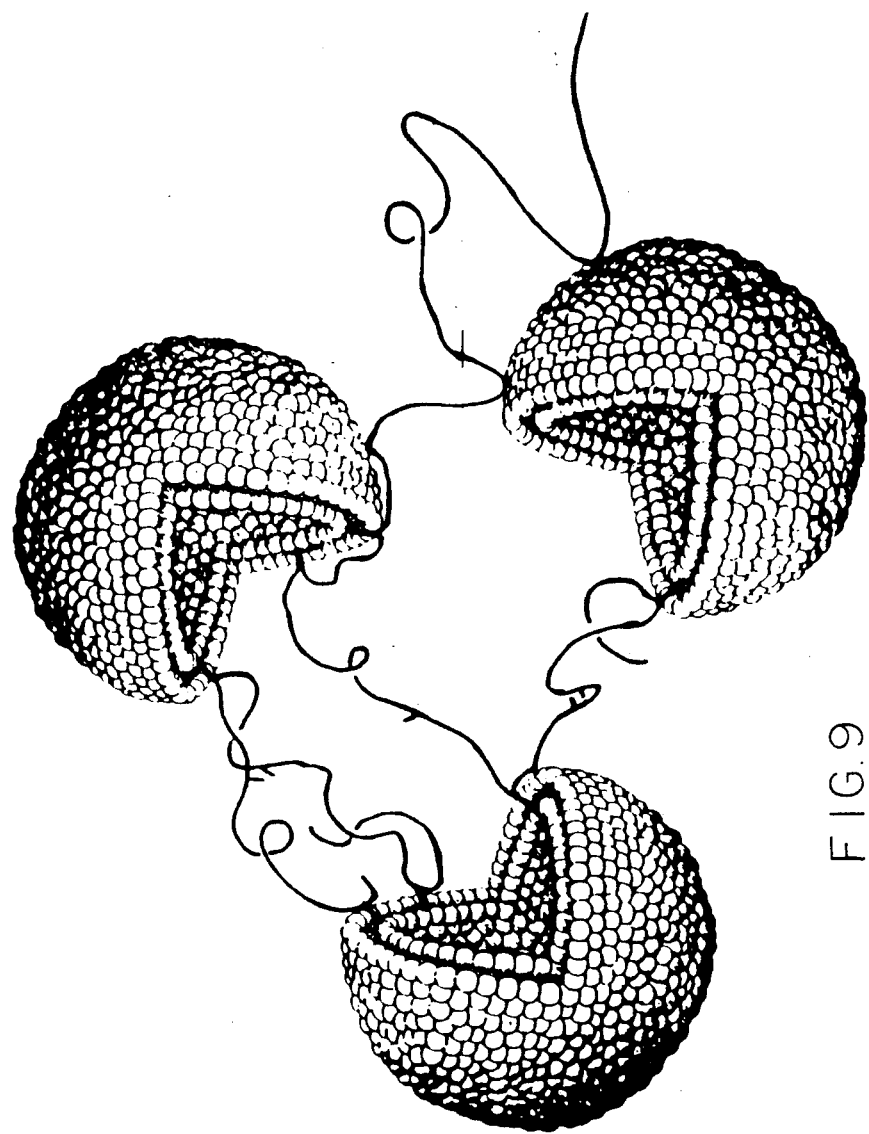
FIG. 9 illustrates a schematic drawing showing the interaction of the polymerizable vesicles with the alkyl-containing polymer in an aqueous media. This drawing also shows the type of three-dimensional networks set up within the solution.

Item 7 can be explained in qualitative terms by assuming that the alkyl groups on the copolymer are compatable with the bilayer structure of the vesicle (see FIG. 9). As a result of this unique interaction and the relatively large separation between these alkyl groups on a chain, "bridging" occurs between vesicle via the polymer chain. This "networking" effect produces large structures that are able to span larger distances. This increase in size, in turn, produces the rise in viscosity.

Figure 10A:
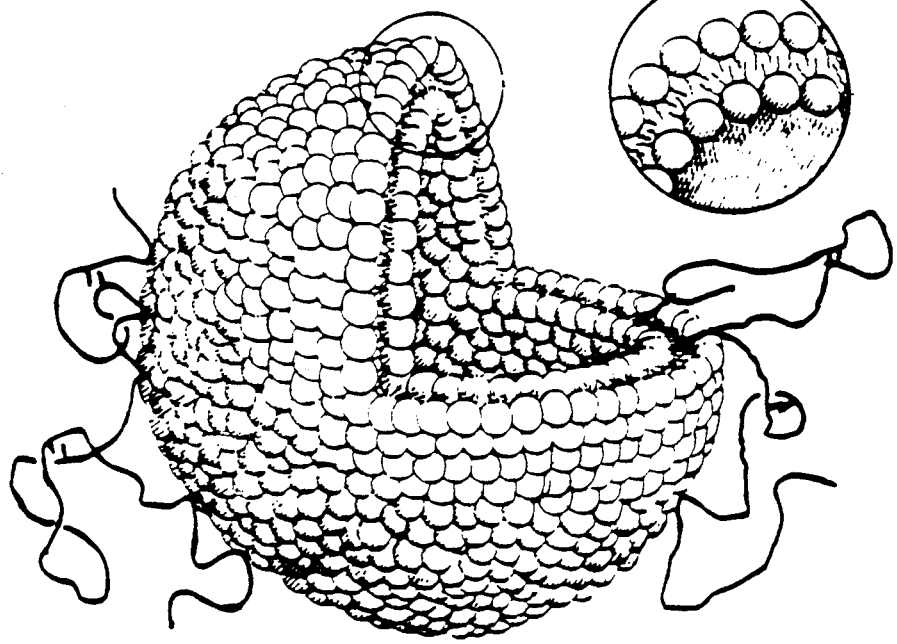
FIG. 10 illustrates a schematic drawing showing the interaction of a polymerizable vesicle with the alkyl-containing polymer in an aqueous media. This drawing also shows that under these conditions, a three-dimensional network is not formed but the vesicle becomes "coated" with the interacting polymer.
Figure 10B:
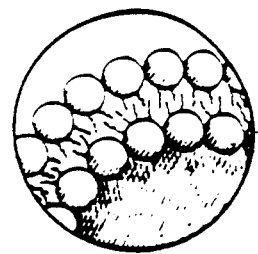

Item 8 can be explained in qualitative terms by assuming that the alkyl groups on the copolymer are compatible with the bilayer structure on essentially one vesicle only (see FIG. 10). Since the "bridging" mechanism is for the most part not a dominant structural feature within the fluid, little increase in viscosity is noted. In essence, the copolymer "coats" the vesicle surface with only a relatively modest change in dimensions, in this specific instances. This unique structure of colloidal vesicle and "compatable" polymers is of both scientific and technological interest.

Again in summary, the synthesis, preparation and utilization of mixtures of polymerizable vesicles formed via anionic/cationic interactions and alkyl-containing polymers and fluid compositions can impart improved and useful rheological properties of aqueous fluids. The specific properties can be varied over a very broad range due to the ability to readily modify or change a number of compositional variables within the monomer comprising the monomer mixture and polymer structures.

Again these types of monomer containing aqueous viscoelastic fluids are useful as rheological control additives in a variety of drilling operations. Included in this category are a variety of well control and workover fluids, fracturing fluids, brine vicosifiers, gelation agents, foaming additives, completion fluids, enhanced oil recovery, drag reduction agents and the like. In addition, these vesicle-containing fluids are excellent candidates for a variety of encapsulation procedures encompassing oil field chemical applications, drug delivery, fertilizer encapsulation and the like.

What is claimed is:

1. An aqueous solution comprising
   (a) water
   (b) about 0.1 to about 20.0 wt.% of a mixture of a viscoelastic monomer fluid and an anionic-alkyl containing copolymer, wherein said viscoelastic monomer fluid is a mixture of a cationic monomer and an anionic monomer characterized by the formula:

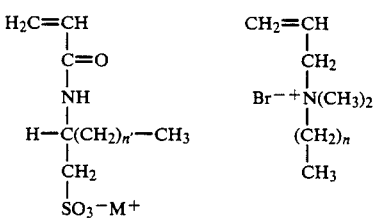

wherein n′ and n are 6 to 22 and a ratio of the cationic monomer to the anionic monomer is about 1.1/1 to 1/1.1; wherein the anionic alkyl containing copolymer is characterized by the formula:

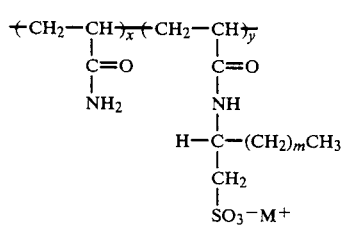
wherein m is 6 to 22 and y is about 10.0 to about 0.1 mole %, and M is a tertiary amine or a metal cation selected from the group consisting of aluminum, lead and Groups IA, IIA, IB and IIB of the Periodic Table of Elements, wherein the weight ratio of the viscoelastic monomer fluid to the anionic alkyl containing a polymer is about 1.1/1 to 1/1.1.
* * * * *